United States Patent [19]
Whitmore, III et al.

[11] Patent Number: 5,931,786
[45] Date of Patent: Aug. 3, 1999

[54] ULTRASOUND PROBE SUPPORT AND STEPPING DEVICE

[75] Inventors: Willet F. Whitmore, III; Winston E. Barzell; Roger F. Wilson, all of Sarasota, Fla.

[73] Assignee: Barzell Whitmore Maroon Bells, Inc., Sarasota, Fla.

[21] Appl. No.: 09/095,563

[22] Filed: Jun. 11, 1998

Related U.S. Application Data

[63] Continuation-in-part of application No. 08/944,752, Oct. 6, 1997, abandoned, which is a continuation-in-part of application No. 08/876,047, Jun. 13, 1997, abandoned.

[51] Int. Cl.⁶ ................................................. A61B 3/00
[52] U.S. Cl. ............................................................ 600/459
[58] Field of Search .................................... 600/459, 462, 600/463, 464

[56] References Cited

U.S. PATENT DOCUMENTS

| | | | |
|---|---|---|---|
| 4,742,829 | 5/1988 | Law et al. ............................... | 128/660 |
| 5,178,148 | 1/1993 | Lacoste et al. ...................... | 128/660.03 |
| 5,398,690 | 3/1995 | Batten et al. ........................ | 128/662.05 |
| 5,474,071 | 12/1995 | Chapelon et al. .................. | 128/660.03 |
| 5,494,039 | 2/1996 | Onik et al. .......................... | 128/662.05 |

OTHER PUBLICATIONS

B & K User Guide for the Stepping Unit UA 1084, Oct. 1994.
"Martin" Immobilization Device, Catalog #9102–MA, Mick Radio–Nuclear Instruments, Inc.
Northwest Transperineal Prostate Implant Stabilization Device, Transperineal Prostate Implant Dosimetry Service.
"Cotan" Stabilizing Device, Catlog #8812–C, Mick Radio––Nuclear Instruments, Inc.
Stabilizer, Hutchinson Medical Designs.
"Ultrasound Transducer Covers and Needle Guides," brochure of Civco Medical Instruments, Kalona, Iowa 52247.
"Brachytherapy Ultrasound System," brochure of Carolina Medical Inc., King, NC 27021–0307.

*Primary Examiner*—George Manuel
*Attorney, Agent, or Firm*—Pennie & Edmonds LLP

[57] ABSTRACT

Apparatus for a medical instrument includes bracket member having a cavity dimensioned and configured to receive at least a portion of the medical instrument; carriage member defining a recess adapted to rotationally support the bracket member; base assembly adapted to be slidably connected to support the carriage member; grid support member adapted to be connected to one end of the base assembly; and template grid, coupled to the grid support member, the template grid having a plurality of grid apertures. In one preferred embodiment, the medical instrument is an ultrasound probe.

14 Claims, 9 Drawing Sheets

ULTRASOUND PROBE SUPPORT AND STEPPING DEVICE

CROSS-REFERENCE TO RELATED APPLICATIONS

This is a continuation-in-part of application Ser. No. 08/944,752 filed on Oct. 6, 1997, now abandoned which is a continuation-in-part of application Ser. No. 08/876,047 filed on Jun. 13, 1997, now abandoned.

BACKGROUND ART

This invention relates generally to support apparatus for precision medical instruments, and more particularly to an adjustable support and stepping device for use with transrectal ultrasound imaging probes and a template grid or matrix used in brachytherapy for cancerous prostate and other transrectal ultrasound probe surgery.

The American Cancer Society estimated that there were 317,000 American men diagnosed with prostate cancer in 1997. Traditional treatment with radiation and surgery are associated with significant side effects and one currently widely applied and popular method for the treatment of prostate cancer is the percutaneous transperineal implantation of radioactive seeds of either Iodine-125 or Palladium-103 called brachytherapy. This procedure is performed with the patient in the lithotomy position, using an ultrasound imaging probe placed in the rectum to monitor seed placement. A template grid arrangement, which is kept in precise linear orientation with the ultrasound probe, must be accurately oriented adjacent to the perineum in relation to the prostate, and locked in position throughout the procedure to achieve optimum seed placement. Precise and reproducible orientation and positioning of the ultrasound imaging probe in the rectum is a key element in both the calculations required for determining the number and distribution of radioactive seeds required for treatment and their subsequent placement using preloaded needles guided by the perineal template and real time ultrasound imaging.

This form of treatment for prostate cancer has been increasing in popularity because of minimal patient morbidity compared to other available treatments and the potential for improved efficacy due to increasingly accurate methods of seed placement.

Presently, there are many homemade and commercially available devices for mounting, stepping and rotating the various commercially available transrectal ultrasound imaging probes designed for use in this procedure. None of these devices have achieved wide acclaim because of significant limitations in their ease of use and level of precision probe control and placement.

The present invention provides a template grid support or mount, and an ultrasound probe support with a stepping function for precision axial longitudinal movement and rotation of an ultrasound probe. Collectively, this invention is referred to as a stepper. During this procedure of brachytherapy, the ultrasound probe is manually inserted into the rectum and, once the desired orientation is achieved as viewed and confirmed by the monitored ultrasound images, the probe is connected to the stepper (which is typically attached to a support stand). Alternatively, if the support stand has suitable mobility, the stepper and probe can be attached to the support stand before insertion into the rectum. With the support stand set in a fixed mode, a range of positively controlled microadjustments available with some support stands may be used to achieve an ideal probe or instrument orientation for starting the procedure.

The template grid mount supports a needle guiding template grid which may be moved longitudinally along the centerline axis of the ultrasound probe while keeping a constant radial distance from this same axis. The stepping function allows precise, independent, and reproducible longitudinal movement of the ultrasound probe while keeping it in accurate radial position in relation to the grid. The rotation function of the stepper permits free axial rotation of the ultrasound probe and easy placement and removal of the ultrasound probe from the stepping device while retaining position of the stepping function and the template grid.

With a satisfactory starting image obtained, the stepper is used to guide the ultrasound probe and obtain transverse step section images. Seed implantation is achieved by passing seed containing needles through the template grid mounted on the template grid support. Direct ultrasound visualization of seed placement is achieved by utilizing the available movements of the stepper.

SUMMARY OF THE INVENTION

The apparatus for guiding a medical instrument according to the present invention includes a bracket member having a cavity dimensioned and configured to receive at least a portion of a medical instrument; a carriage member defining a recess adapted to rotationally support the bracket member; a base assembly adapted to be slidably connected to support the carriage member and to move the carriage member into an imaging position; and a quick release member operatively associated with the bracket and carriage members for removably attaching and detaching the bracket member to and from the carriage member when the carriage member is in the imaging position without losing the position and orientation of the carriage member.

In one embodiment, the apparatus further comprises a grid support member adapted to be connected to a first end of the base assembly and a template grid having a plurality of grid apertures and being removably coupled to the grid support member. Preferably, the template grid includes first and second spaced surfaces with apertures in the first surface aligned with apertures of the second surface and each aperture is configured and dimensioned to guide elongated objects from the apertures of the first plate to those of the second plate. Additionally, each aperture can be configured to have a wider circumference on one side of the plate to guide the elongated objects.

In another embodiment, a second end of the base assembly includes a handle for changing the position of the grid support member and the template grid. Preferably, the base assembly includes first and second crossbars; first and second elongated, spaced parallel, substantially coextensive sliding rods secured from relative movement by the grid support member and the handle, the first rod being slidable through the first aperture of the first crossbar and the first aperture of the second crossbar and the second rod being slidable through the second aperture of the first crossbar and the second aperture of the second crossbar; an elongated toothed rack connected at opposite ends thereof to the first and second crossbars, the toothed rack slidably engaged with the carriage and being operably engaged with a rotatable gear mounted in the carriage whereby the carriage is moved linearly along the rods and then precisely held in a selected position along the rods in response to rotation of the gear. In a preferred embodiment, the rack includes a plurality of spaced dimples and the carriage member includes at least one spring loaded plunger so that the spaced dimples interact with the spring loaded plunger to identify by feel movement of the carriage member. In another preferred embodiment, the base assembly includes means for eliminating backlash between the carriage member and the base assembly which comprise at least one height adjusting member to move the rack to vary pressure between teeth of the rack and the gear.

In another embodiment, the bracket member includes at least one detent member adapted to rotationally align the bracket member with a longitudinal groove or indent in the medical instrument. The base assembly can include at least one scale to provide indicia of displacement of the carriage member along the base assembly. Additionally, the carriage member can include at least one scale to provide indicia of rotational displacement of the bracket member.

In another embodiment, the base assembly further comprises a base member which is configured and dimensioned for connection to a support stand.

In a final embodiment, the quick release member comprises a grooved portion of the carriage member and a tongued portion of the bracket member. The grooved portion is configured and dimensioned to receive the tongued portion and the tongued portion is releasable from the grooved portion by rotation of the bracket member with respect to the carriage member.

BRIEF DESCRIPTION OF THE DRAWINGS

The present invention is described in detail below with reference to the drawings in which.

DETAILED DESCRIPTION OF THE PREFERRED EMBODIMENTS

In the description which follows, any reference to either direction or orientation is intended primarily and solely for purposes of illustration and is not intended in any way as a limitation to the scope of the present invention. Also, the particular embodiments described herein, although being preferred, are not to be considered as limiting of the present invention.

Figure 1:
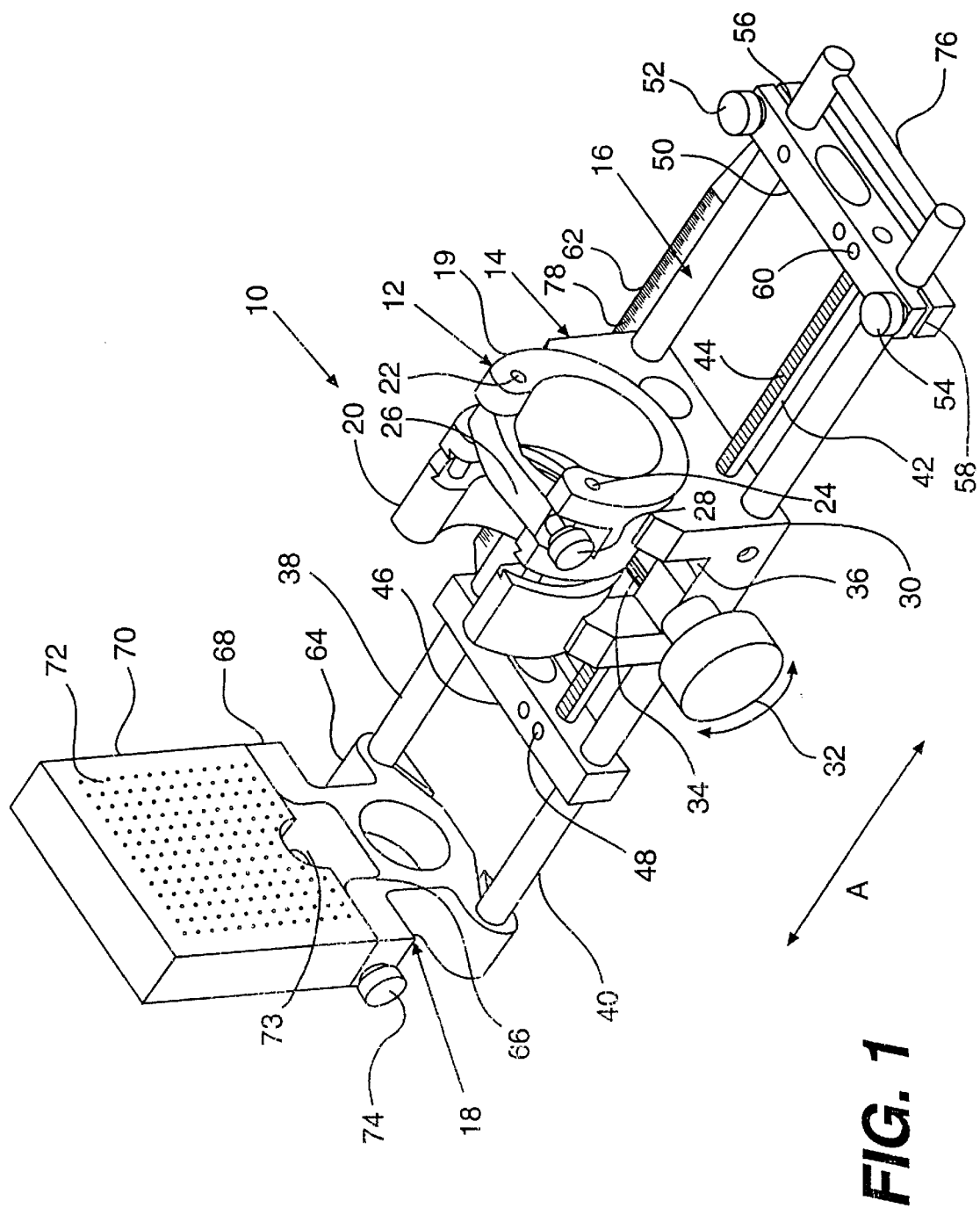
FIG. 1 is a perspective view of one embodiment of the ultrasound probe mount and stepping device according to the present invention, wherein the ultrasound probe mount is in a neutral position.

As shown in FIG. 1, the device 10 of the present invention includes an ultrasound probe mount 12, a carriage 14, a base assembly 16, and a template grid mount 18. The probe mount 12 is adapted to receive and securely clamp around a central enlarged portion of an ultrasound probe. This probe mount 12 is held for rotation within carriage 14. The carriage 14 is, in turn, held for slidable longitudinal movement along the base assembly 16 and the template grid mount 18 is adapted to supportively secure a template grid 70 thereatop.

All of the components of the present device 10 can be made from metal. According to one preferred embodiment, the components can be machined. Preferably, the rails 38 and 40, as described herebelow, can be made of aluminum. Alternatively, many of the components can be fabricated or cast of a plastic, with engineering thermoplastics, such as DELRIN, being exemplary. Nylons, polycarbonates and like materials can be used, if desired.

Figure 2:
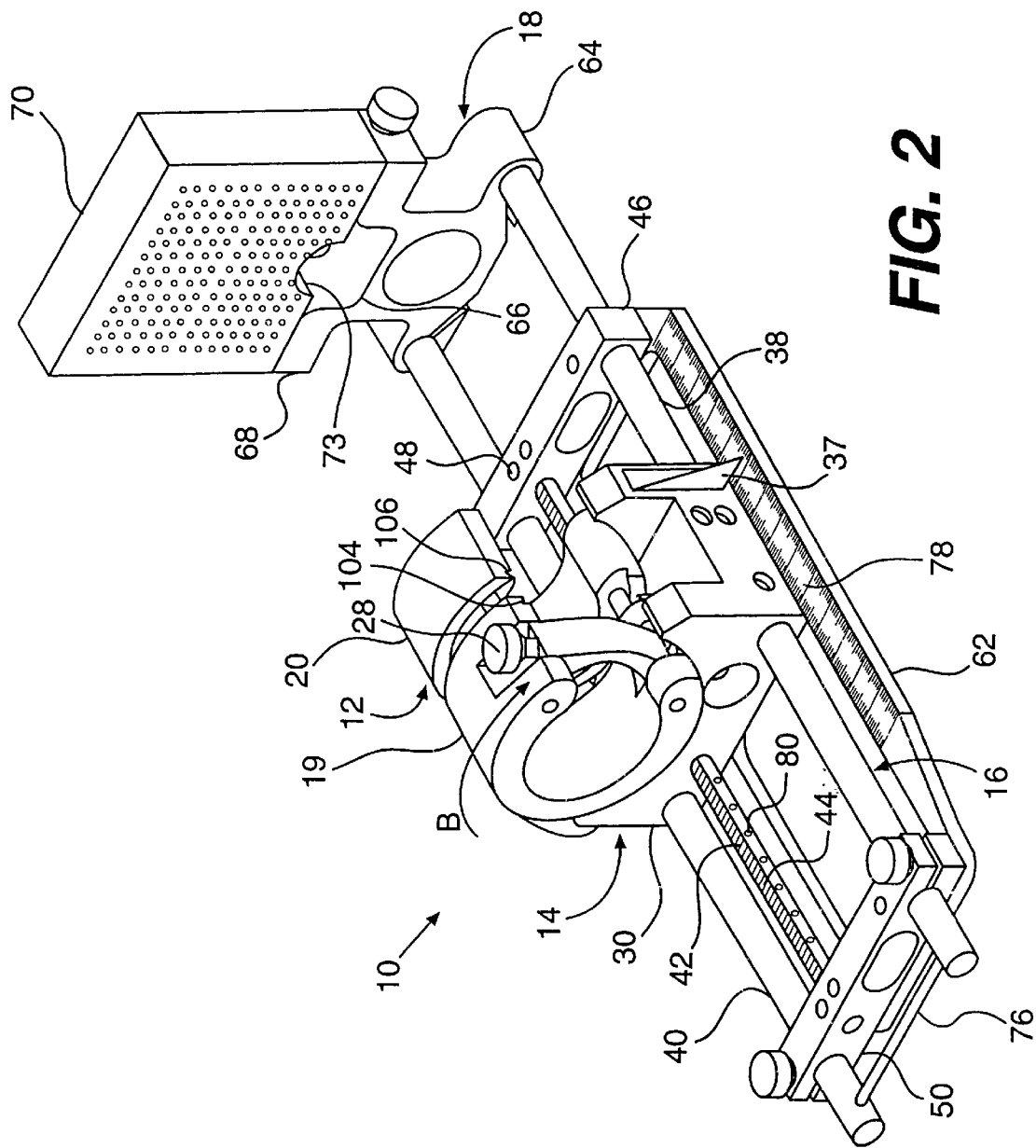
FIG. 2 is a perspective view of the ultrasound probe mount and stepping device of FIG. 1 showing the ultrasound probe mount rotated through 90 degrees clockwise as viewed from the neutral position shown in FIG. 1.
Figure 3:
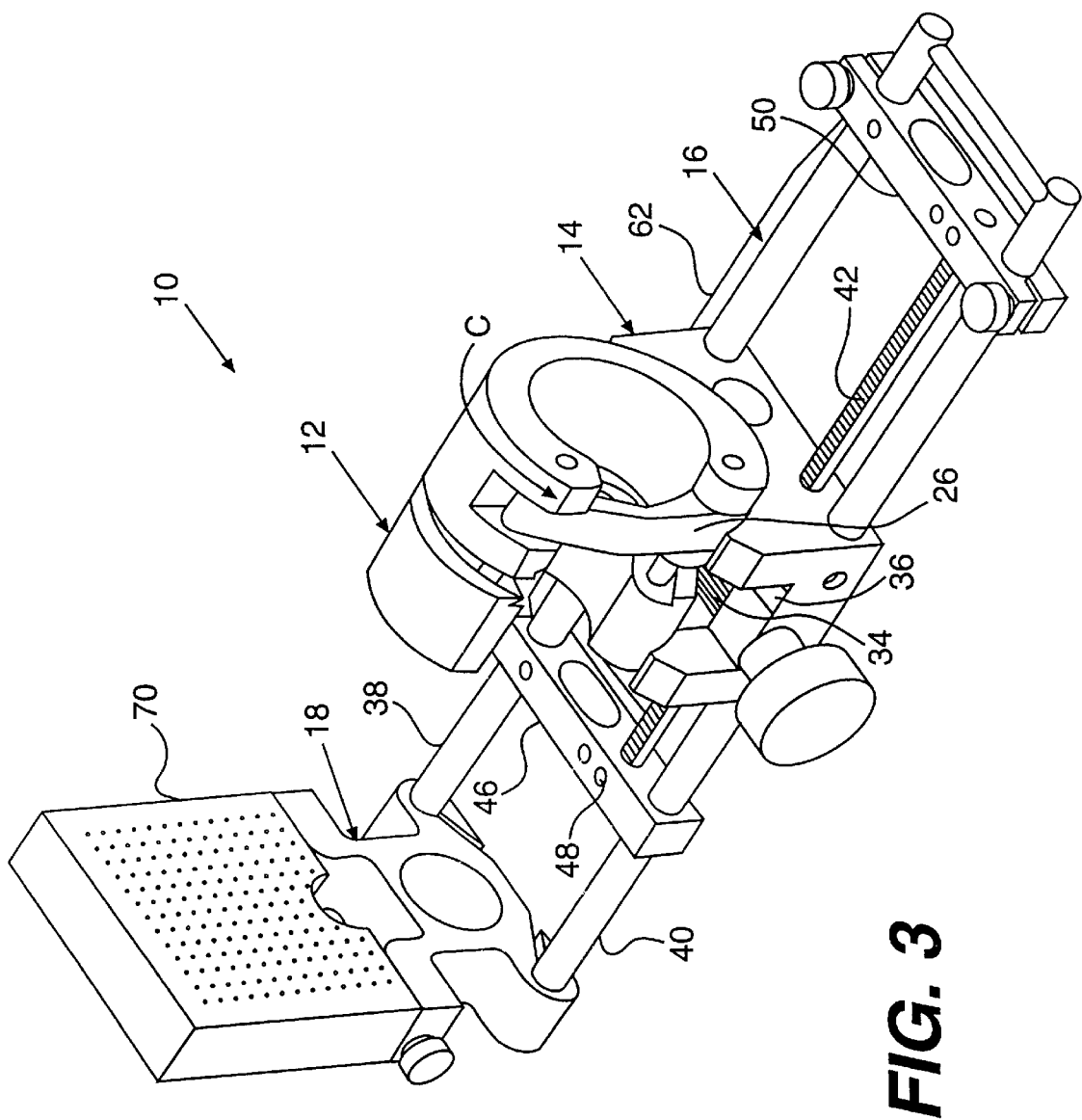
FIG. 3 is a perspective view of the ultrasound probe mount and stepping device of FIG. 1 showing the ultrasound probe mount rotated through about 90 degrees counterclockwise with respect to the neutral position shown in FIG. 1.

With more specific detail of the components of the invention 10 discussed herebelow, and referring additionally to FIGS. 2 and 3, the ultrasound probe mount 12 (with ultrasound probe removed) is manually rotatable against an adjustable friction member back and forth in the direction of arrows B and C through about 90 degrees rotation in either direction from the neutral position of the ultrasound probe mount 12 shown in FIG. 1. As seen in FIG. 3, a cavity 36 is provided as clearance for tightening knob 28 which secures a pivotally connected closure strap 26 for securement of the ultrasound probe therewithin as described more fully herebelow. By this arrangement, the ultrasound probe mount 12 is fully rotatable through about 180 degrees of movement from one extreme to the other. Tightening knob 28, closure strap 26, and probe mount 12 are configured to allow device 10 to be used with ultrasound probes of different sizes, shapes, and manufacture.

The grid mount, as best seen in FIG. 1, is structured for securely clamping and engaging the ends of spaced apart, parallel rails 38 and 40, by lower split flanges 64 which include holes for secure clamping engagement therebetween. The upper flange 68 includes manually tightenable fasteners 74 (typical) on each end thereof for clamping engagement with the template grid 70. A clearance aperture formed by groove 66 in the grid mount 18 and groove 73 formed at the bottom of the template grid 70 provide for clearance access for the elongated sensing portion of the ultrasound probe.

The template grid 70 includes an array of apertures 72 which are precisely arranged and positioned vertically and laterally in a precise manner with respect to the longitudinal axis of the ultrasound probe when it is held within the probe mount 12. These apertures 72 are longitudinally aligned with respect to the device 10 and are sized to receive and precisely align a needle passing therethrough having one or more spaced radioactive pellets held inside the tip of the needle. From the real time ultrasound image produced, in combination with particularly selected apertures 72, a highly accurate placement of the radioactive seeds in the cancerous prostate is achievable.

Figure 5:
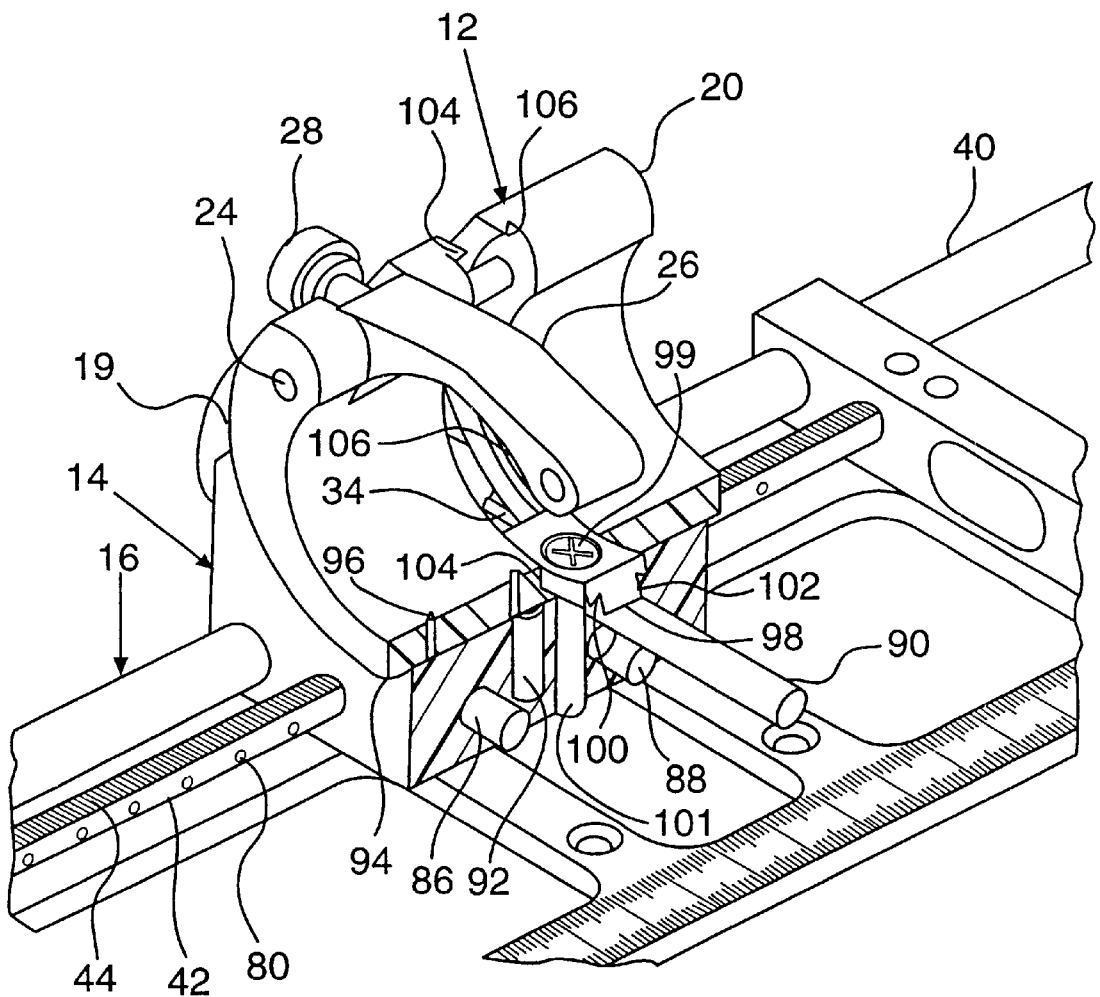
FIG. 5 is an enlarged perspective view in partial section of the ultrasound mount and carriage of the stepper of FIG. 1.
Figure 6:
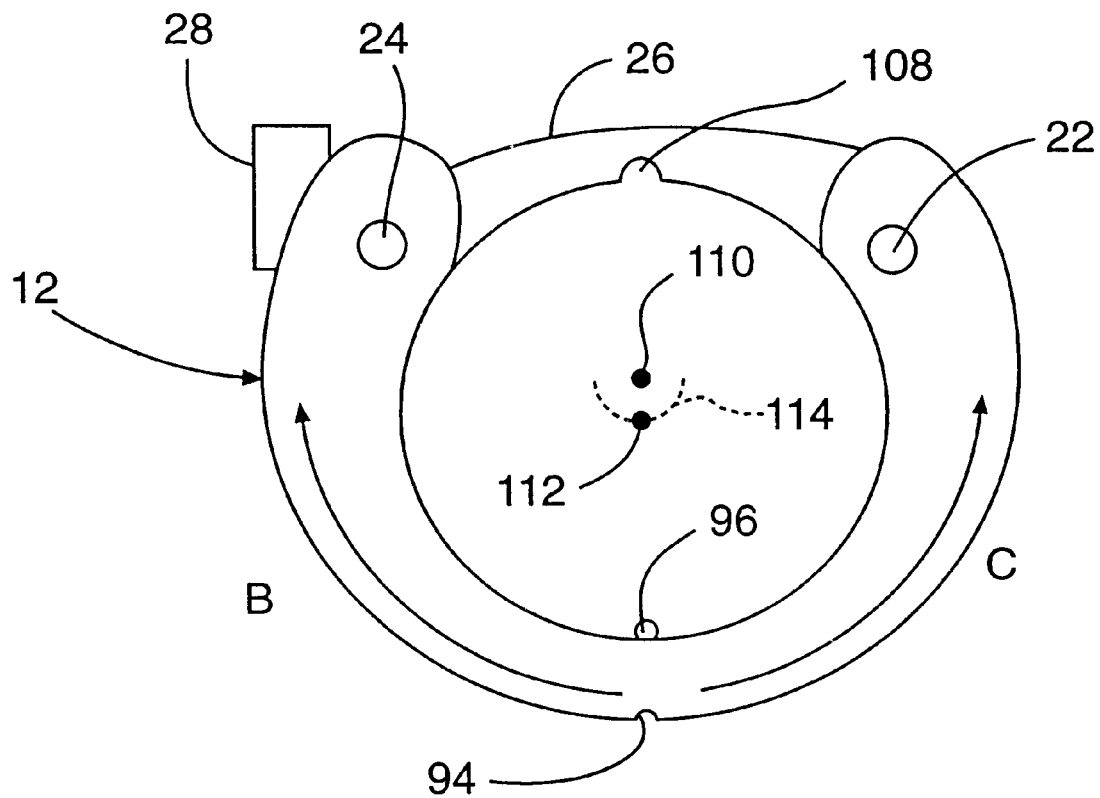
FIG. 6 is an elevation view of one end of the ultrasound probe mount.

Referring now to FIGS. 5 and 6, the details of the probe mount 12, the carriage 14 and the base assembly 16 are shown. The probe mount 12 comprises two generally u-shaped members 19 and 20 which are held spaced apart by longitudinally oriented stainless steel pins 22 and 24. The closure strap 26 is pivotally connected to pin 22, the opposite end of closure strap 26 being structured for locking tightenable engagement by adjusting knob 28 with structure of the corresponding end of u-shaped channel member 19.

The closely spaced facing edges of the u-shaped members 19 and 20 have a dovetail groove 104 and 106 which mateably and trappingly engages with a corresponding dovetail shape of a locking block 98. The locking block 98 is connected to the carriage 14 by a flush mounted threaded fastener 99 which threadably engages into a threaded nylon insert 101 connected within carriage 14 as seen in FIG. 5. The upwardly facing concave contour of locking block 98 generally conforms with the cylindrical aligned inner surfaces of each of the u-shaped members 19 and 20. By this arrangement, the probe mount 12 is rigidly secured within carriage 14 for rotational movement only with the frictional resistance to rotational movement controlled by the tensioning of threaded fastener 99 against locking block 98.

One benefit of this structural arrangement of the probe mount 12 is to allow for at least −90° to +90° movement back and forth in the direction of arrows B and C from a neutral position of the probe mount 12 not presently available in any earlier known device. This neutral position is physically identified by providing a detent ball plunger 92 mounted uprightly within carriage 14 and interacting with a longitudinal groove or other suitable depression 94 formed centrally along the lower outer surface of the probe mount 12. Proper alignment of the ultrasound probe is initially established by providing one or more protuberances 96 which upwardly extend from the inner surface of the u-shaped members 19 and 20. These protuberances 96 interact with a longitudinal groove or other suitable depression formed in most, if not all, ultrasound probe units for identifying a design orientation with respect to the probe mount 12. For probe units having alignment pin(s) rather than a groove or depression, probe mount 12 can be provided with a groove for ensuring alignment.

Referring more specifically to FIG. 6, after the probe is inserted in probe mount 12, the geometric center of the probe is located generally at 112 while the imaging center is located vertically upwardly at 110. In order to compensate for this arrangement, as the probe mount 12 is rotated in the direction of either B or C, the geometric center 112 moves along arc 114 so that imaging center 110 rotates without any lateral displacement.

Another benefit of the structural arrangement of the probe mount 12 and carriage 14 is the ability to remove the probe mount 12 from the carriage 14 by rotation. Because the u-shaped members 19 and 20 do not form a complete circle as shown best in FIGS. 1 and 2, the probe mount 12 can be spun-out or off the carriage 14 until free thereof. This allows for ease of removal of probe mount 12 for cleaning purposes. In addition, this allows the probe mount 12 to be easily replaced with a new unit when inoperative. Such ease of removal and replacement of the probe without loss of position is very desirable during medical procedures should the rectum fill with gas or stool and require cleansing to restore a good ultrasound image.

The base assembly 16 includes two aluminum rails 38 and 40 held in spaced relation at one end by the grid mount 18. The opposite ends of rails 38 and 40 are clampingly engaged into a first transversely oriented crossbar 50 which is clampingly secured by thumb screws 52 and 54 which squeezably engage and reduce the gaps 56 and 58 against the corresponding rails 38 and 40. A separate crossbar 76 is also permanently attached between the corresponding ends of the rails 38 and 40. These crossbars 46 and 50 are connected to and supported by a flat aluminum base plate 62 which is adapted to be secured to a support stand. A preferred support stand for use in this invention is shown in PCT application PCT/US98/01252. The position of template grid mount 18, and consequently template grid 70, is adjustable by moving rails 38 and 40 using crossbar 76 as a handle when thumb-screws 52 and 54 are loosened. The ability to adjust the position of template grid 70 through the back of device 10 is another benefit.

The carriage 14 is slidably engaged around the rails 38 and 40 through moving longitudinal apertures formed through the lower corners of the carriage 14 as best seen in FIG. 1. Alternatively, a single rail can be used if desired. To control the linear longitudinal movement and secure positioning of the carriage 14 back and forth in the direction of arrow A in FIG. 1, an adjusting knob 32 (on one or both sides of carriage 14) rotatable back and forth in the direction of the arrows is connected to a coaxial gear 34 about a transverse axis with respect to the carriage 14 as also partially seen in FIG. 5. An elongated rack 42 having finely spaced straight teeth 44 formed along one surface thereof is connected at one end to the first crossbar 50, the details of that connection described herebelow with respect to FIG. 4. The opposite end of rack 42 is secured within a second transversely oriented crossbar 46. The rack 42 is slidably engageable within a longitudinal aperture formed through carriage 14 and positioned between the longitudinal apertures formed to slidably receive rails 38 and 40.

By this arrangement of gear 34 and stationary rack 44, by rotating the adjusting knob 32 back and forth in the direction of the arrow, movement of the carriage 14 in either direction of arrow A is effected. As best seen in FIGS. 2 and 5, the rack 42 also includes a series of precision spaced laterally facing dimples 80 which interact with spaced spring loaded ball plungers 86 and 88 so as to identify by feel the preselected distance of movement between each felt detent as adjusting knob 32 is rotated to effect movement of the carriage 14. This gear, rack, and detent system achieves the stepping function required during the procedure. An alternative to knowing the exact distance of movement of the carriage 14 is provided by a fixed blade 37 positioned directly above a conventional measuring scale 78 on base plate 62 which can be viewed so as to determine the desired amount of longitudinal movement of the carriage 14.

Figure 4:
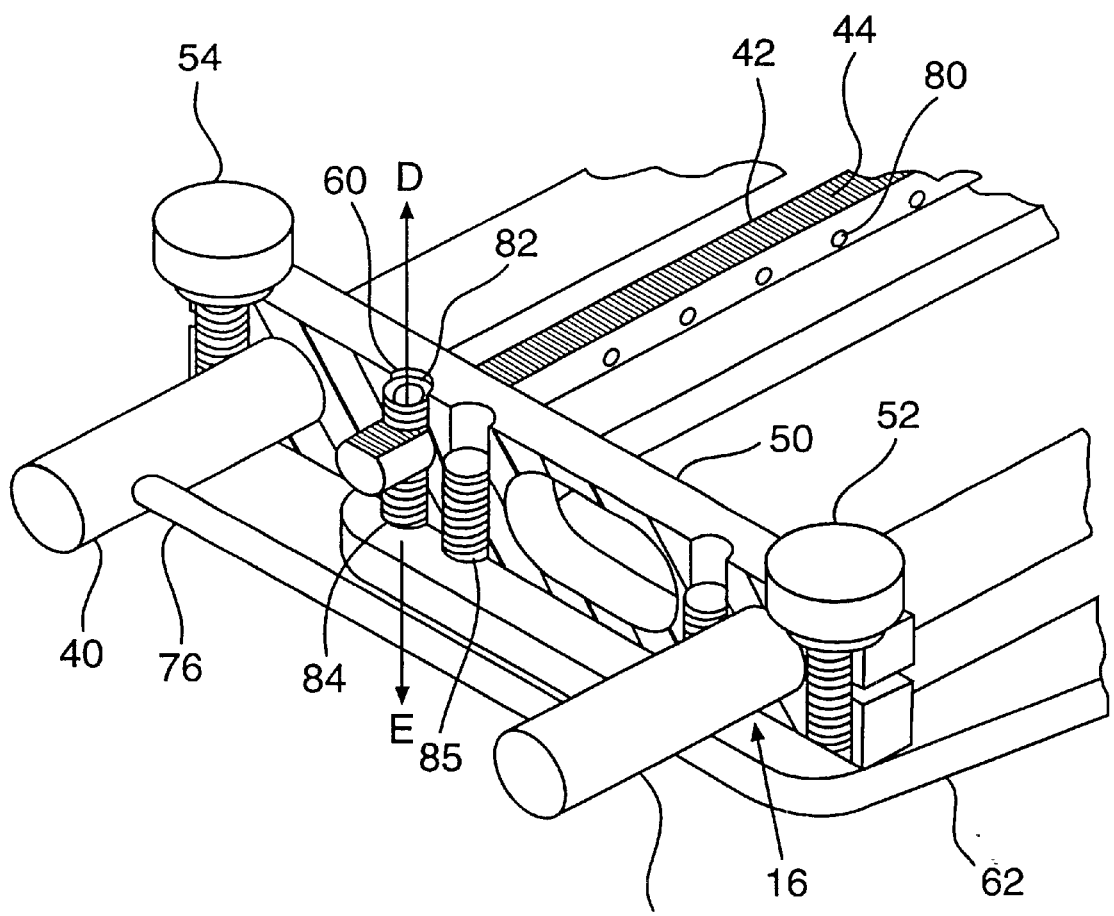
FIG. 4 is an enlarged perspective view in partial section of one end of the stepping device shown in FIG. 1.

Referring now to FIG. 4, a means for eliminating all backlash between gear 34 and the teeth 44 of rack 42 is there shown. One end of the rack 42 extends through the first crossbar 50 and is held in position by set screws 60 and 84 within threaded hole 82. By appropriate vertical repositioning and retightening of the set screws 60 and 84, movement of the end of rack 42 in the direction of arrows D or E, facilitated by an enlarged hole having a larger inside diameter than the outside diameter of rack 42, the pressure exerted by upwardly facing teeth 44 against gear 34 is adjustably controlled. A similar arrangement at the outer end of rack 42 is provided within the crossbar 46 by upper set screw 48 and lower set screw (not shown).

Figure 7:
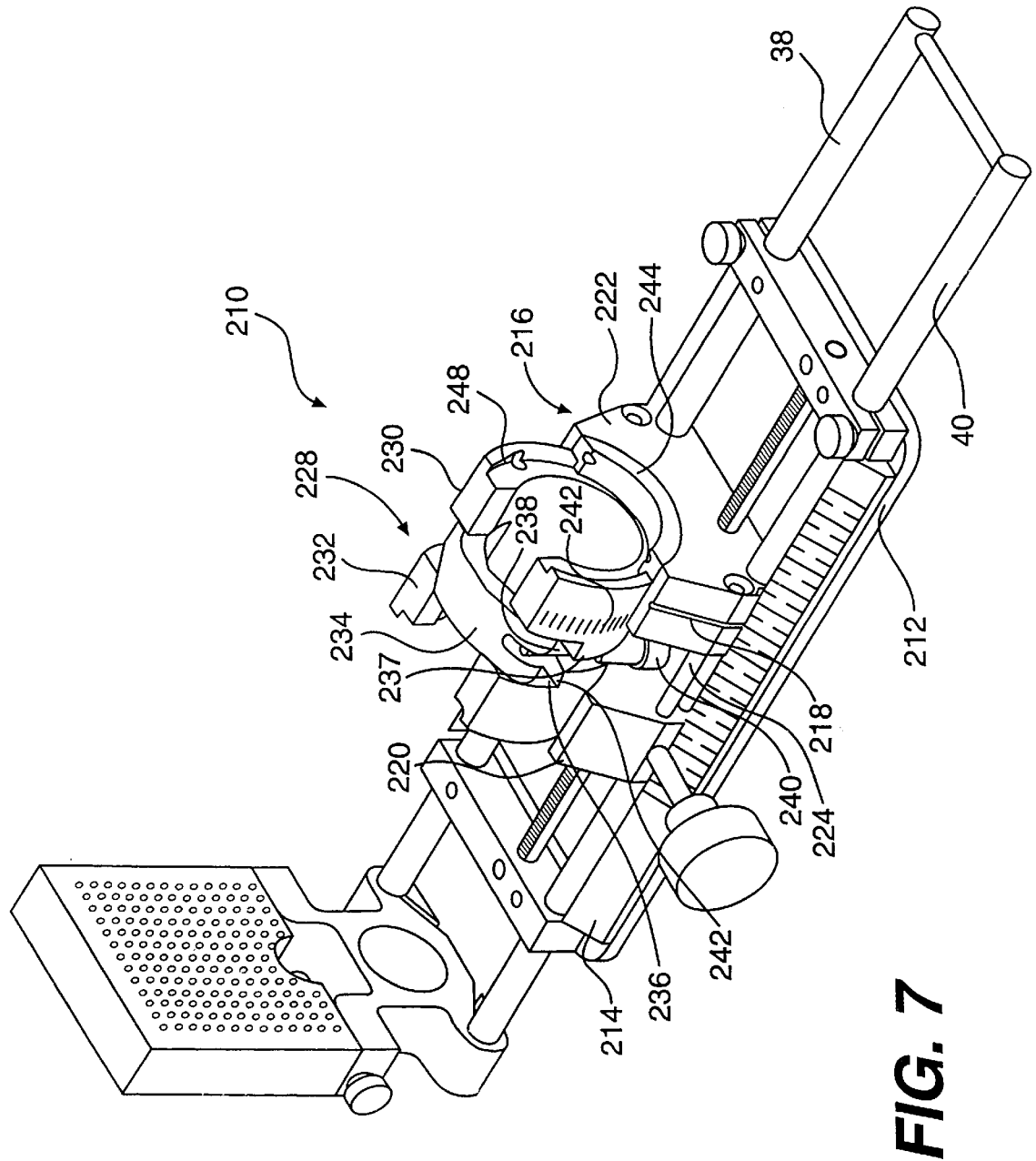
FIG. 7 is a perspective view of another embodiment of the device of the present invention which includes an ultrasound probe mount in a neutral position.
Figure 8:
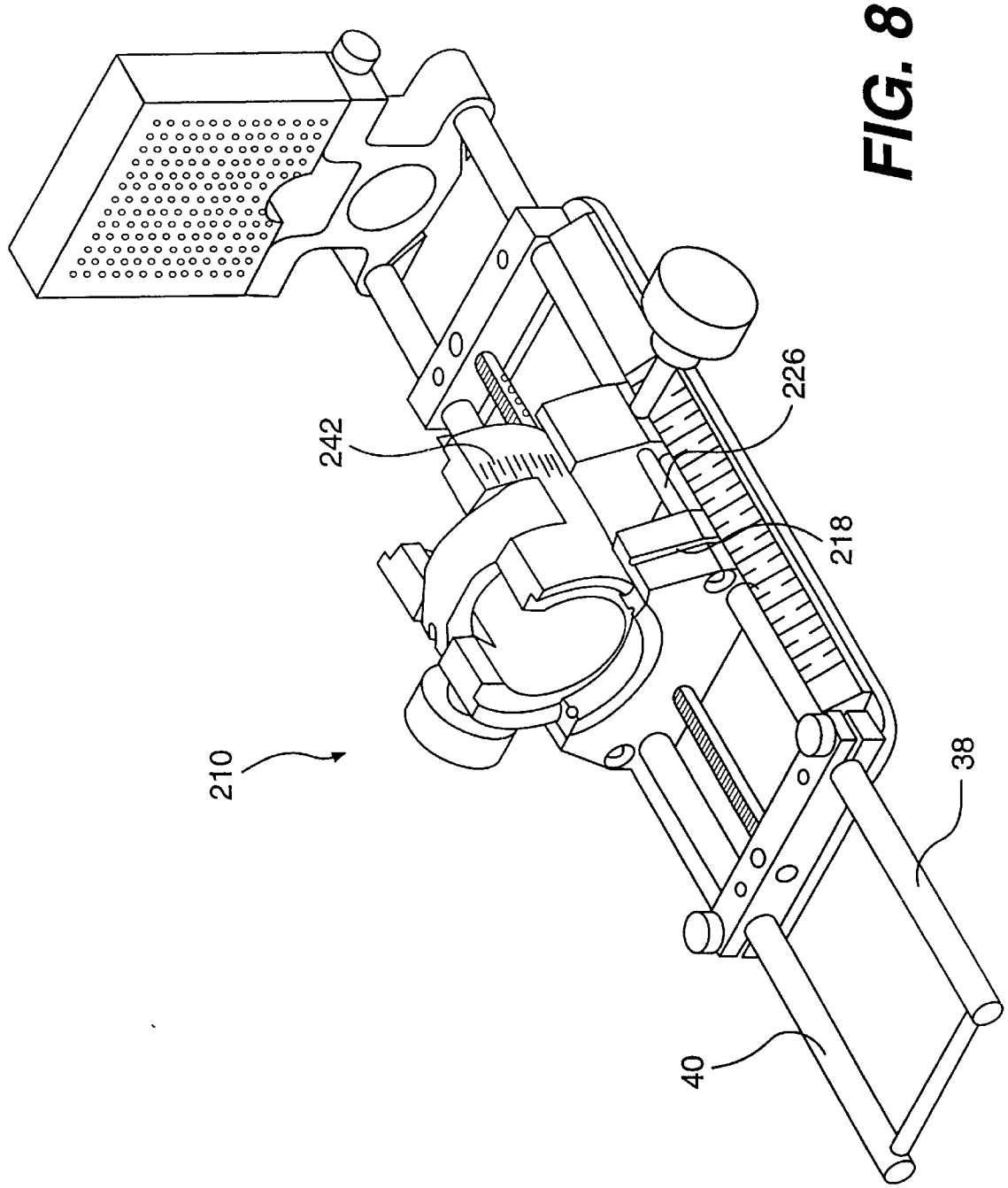
FIG. 8 is a perspective view of the ultrasound probe mount and stepping device of FIG. 7.

Turning now to FIGS. 7 and 8, an alternative embodiment of the device 210 according to the present invention is shown. In general, most of the structure shown in FIGS. 7 and 8 is like or comparable to the structure illustrated in the embodiment shown in previous FIGS. 1 through 6 and accordingly discussion of those like components is not believed necessary. The base plate 212 supports a tilted scale 214 positioned along each elongated side of base plate 212. Preferably the scale 214 is tilted at about forty-five (45) degrees for ease of viewing by the medical personnel using the device of the present invention.

The carriage 216 is formed of two like shaped generally trapezoidal blocks 220 and 222 which are separated and kept apart by pins 224 and 226 as shown in FIGS. 7 and 8. The distance between blocks 220 and 222 is adjustable along pins 224 and 226. Carriage block 220 has an indicator line 218 on each side to match up against the scales 214. As the block moves along rods 38 and 40 the position of the carriage 216 can be measured or determined along either scale 214.

The carriage 216 provides an arcuate recess that accommodates the outer curved portion of a probe mount or cradle 228 which can be formed as an integral piece or bracket with u-shaped members 230 and 232. The closure strap 234 is pinned at one end between u-shaped members 230 and 232 for pivotal rotation thereabout. At its other end the closure strap 234 can be positioned within recess 236 defined between u-shaped members 230 and 232. Recess 236 includes a narrow portion 237. A latch pin 238 is rotationally pinned at its one end to the other end of closure strap 234. The other end of latch pin 238 is coupled to tightening knob 240 which can be rotationally threaded on pin 238. After a probe is positioned within probe mount 228, the closure strap 234 can be placed over a portion of the outer surface of the probe. The free or other end of closure strap 234 is placed in the recess 236, the pin 238 is moved into the narrow portion 237 of recess 236, and the tightening knob 240 is rotated on pin 238 to rest against the lower (not shown) shoulders 242 in recess 236. The tightening knob 240 is thus oriented or positioned so that it does not interfere with the top surface of the cradle or probe mount for needle placement nor does it alter the shape of the probe cradle with clamping pressure. Probe mount 228 and in particular tightening knob 240 and closure strap 234 are configured to accommodate various ultrasound probes. The probe mount or cradle 228 also has rotation scales 242 on each side of u-shaped member 230. If desired, rotation scales 242 can also be placed on the other u-shaped member 232.

Although probe mount 228 can be freely positioned in the arcuate recess of carriage 216 for rotational movement about a longitudinal axis of device 210, in one preferred embodiment slotted or grooved guides 244 and 246 are secured by known techniques at upper end portions of carriage 216. The guides 244 and 246 have generally L-shaped cross-sections which fit over corresponding L-shaped grooves 248 in the ends of probe mount 228 which is thus rotationally secured to carriage 216. In this embodiment, the locking block 98 with dovetail grooves 100 and 102 and corresponding mating structures on probe mount 12 are not needed. It is believed that the probe mount 228 is more stably retained in its rotational configuration relative to carriage 216. In addition, because the u-shaped members 230 and 232 do not form a complete circle as shown in FIGS. 7 and 8, the probe mount 228 can be spun-out or off the carriage 216 until free thereof. This allows for ease of removal of probe mount 228 for cleaning purposes. In addition, this allows any broken or worn out probe mount 228 to be easily replaced with a new unit. Such ease of removal and replacement of the probe without loss of position is very desirable during medical procedures should the rectum fill with gas or stool and require cleansing to restore a good ultrasound image.

The device of the present invention exemplified in devices 10 and 210 is called a BRACHYSTEPPER, and is a lightweight, state of the art, precision stepping device which is ideally matched to a portable stand known as the BRACHYSTAND, which is described and illustrated in PCT application PCT/US98/01252, and is adaptable to a variety of commonly used ultrasound brachytherapy systems.

The features of these devices according to the present invention include: lightweight, improving the "feel" and safety when manipulating the probe in the rectum; firm and positive stepping function preventing slippage; easy to read carriage scales from either side by medical personnel including both surgeon and assistant; rotational capability of at least 180 degrees with easy to read marking scales from either side; audible and palpable secure centerline detent featuring smooth, clockwise and counterclockwise rotation; grid movement independent of the ultrasound probe controlled from a convenient backside location; standard template grid for either 17 gauge or 18 gauge needles spaced in 5 mm increments with graphics and elevations specific for each brand of ultrasound (custom grid configurations can also be employed, as desired); and an open configuration and easy separability of components allowing for convenient cleaning and maintenance.

In use, the BRACHYSTEPPER or devices 10 or 210 can be attached to the BRACHYSTAND. An ultrasound probe can be placed into the BRACHYSTEPPER cradle or probe mount. The probe can be centered in rotation by feeling the centerline detent. The BRACHYSTAND is operated to obtain satisfactory probe position and image for implantation. A dosimetry calculation is performed using the Brachystepper carriage knob and scale. A sterile template grid is placed on the grid platform and positioned appropriately close to the perineum and locked in place with the grid locking knobs. Then the implantation is performed.

By the precision nature of the devices 10 and 210 as above described, it will now be understood that the present invention clearly provides a very precision support for an ultrasound probe and template grid for substantially enhanced accuracy in placing radioactive seeds into a cancerous prostate. By providing fine incremental adjustments of both the linear positioning about the longitudinal axis of the ultrasound probe, and accurately knowing precision spacing between each of the longitudinal apertures 72 in template grid 70 by preestablished dimensional relationships between the probe mount 12, 228, carriage 14, 216, and grid mount 18, the efficacy and ultimate benefits of brachytherapy on cancerous prostates is enhanced. Furthermore, because probe mount 12, 228 can be removed by rotation relative to carriage 14, 216, if the probe or probe mount breaks or needs cleaning during seed implantation, probe mount 12, 228 can be removed from carriage 14, 216 for cleaning, repair, or replacement without affecting the position of carriage 14, 216. Thus, when probe mount 12, 228 is replaced on carriage 14, 216, the probe is in substantially the same position it was in prior to removal.

Figure 9:
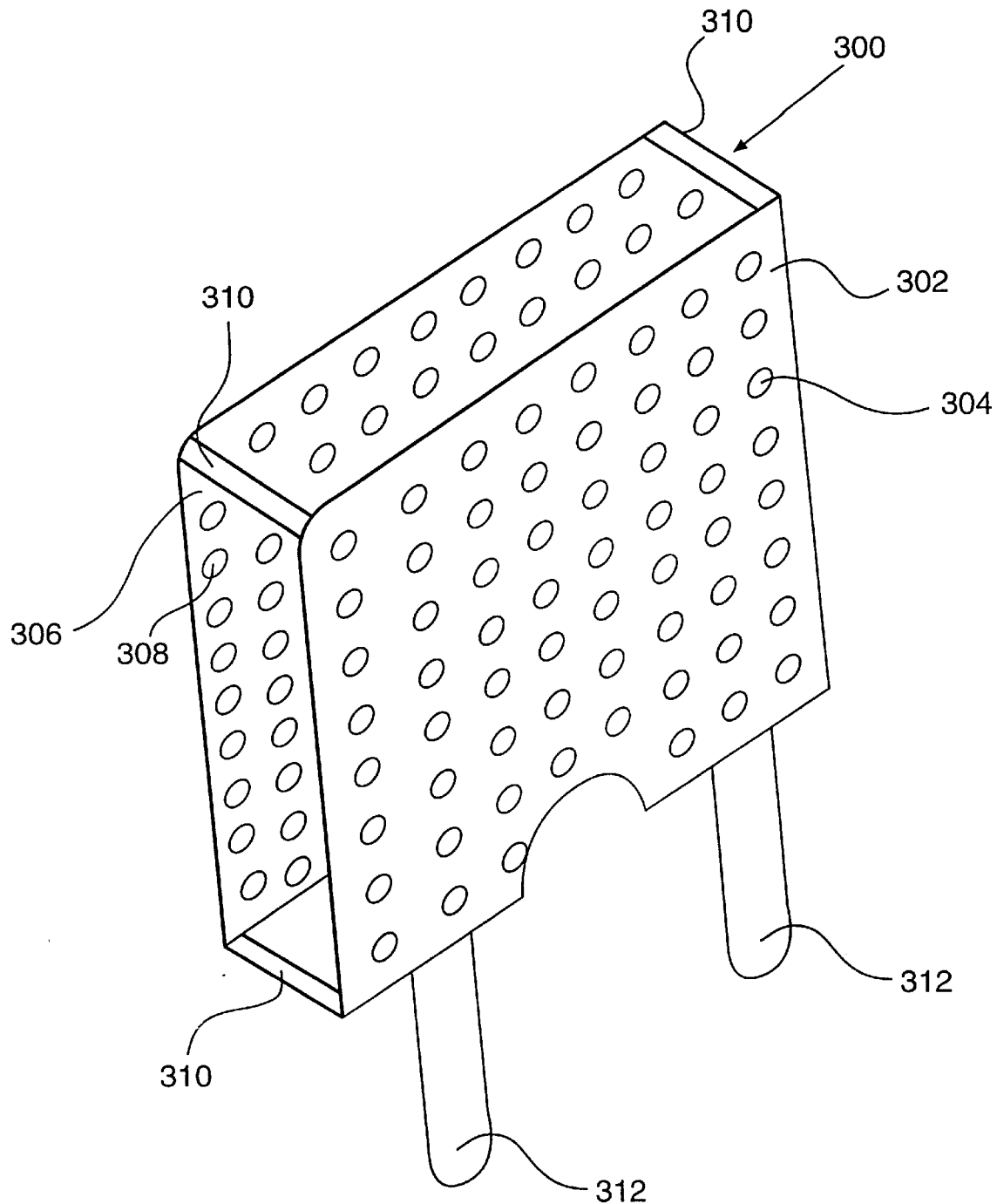
FIG. 9 is a perspective view of another embodiment of a template grid that can be used with the present invention.

FIG. 9 shows another template grid design that can be used with devices 10 and 210. Template grid 300 has a first surface 302 having apertures 304 and a second surface 306 having apertures 308. Bars 310 connect first 302 and second 306 surfaces so that apertures 304 and 308 align to allow implants, such as the radioactive seed-containing needles, to pass from apertures 304 to apertures 308. Apertures 304 and 308 can be configured to have a wider circumference on one side surface to help guide the implants. Prongs 312 are for connecting template 300 to grid mount 18. Additional preferred embodiments of template grids for use with device 10 and 210 are disclosed in the inventors' co-pending application Ser. No. 09/085,011 entitled "Sterile Disposable Template Grid System" and filed May 28, 1998, the content of which is hereby incorporated by reference.

While the instant invention has been shown and described herein in what are conceived to be the most practical and preferred embodiments, it is recognized that departures, modifications, adaptations and variations may be made therefrom within and without departing from the scope of the invention, which is therefore not to be limited to the details disclosed herein, but is to be afforded the full scope of the claims so as to embrace any and all equivalent apparatus and articles.

What is claimed is:

1. An apparatus for guiding a medical instrument comprising:
   a bracket member having a cavity dimensioned and configured to receive at least a portion of a medical instrument;
   a carriage member defining a recess adapted to rotationally support the bracket member;
   a base assembly adapted to be slidably connected to support the carriage member and to move the carriage member into an imaging position; and
   a quick release member operatively associated with the bracket and carriage members for removably attaching and detaching the bracket member to and from the carriage member when the carriage member is in the imaging position without losing position and orientation of the carriage member,
   wherein the quick release member comprises a grooved portion of the carriage member and a tongued portion of the bracket member, the grooved portion configured and dimensioned to receive the tongued portion and the tongued portion releasable from the grooved portion by rotation of the bracket member with respect to the carriage member.

2. The apparatus of claim 1 wherein the apparatus further comprises a grid support member adapted to be connected to a first end of the base assembly; and a template grid having a plurality of grid apertures and being removably coupled to the grid support member.

3. The apparatus of claim 2 wherein a second end of the base assembly includes a handle for changing the position of the grid support member and the template grid.

4. The apparatus of claim 2 wherein the template grid includes first and second spaced surfaces with apertures in the first surface aligned with apertures of the second surface.

5. The apparatus of claim 4 wherein each aperture is configured and dimensioned to guide elongated objects from the apertures of the first surface to those of the second surface.

6. The apparatus of claim 1 wherein the bracket member includes at least one detent member adapted to rotationally align the bracket member with a longitudinal groove or indent in the medical instrument.

7. The apparatus of claim 1 wherein the base assembly includes at least one scale to provide indicia of displacement of the carriage member along the base assembly.

8. The apparatus of claim 1 wherein the base assembly includes means for eliminating backlash between the carriage member and the base assembly.

9. The apparatus of claim 1 wherein the carriage member includes at least one scale to provide indicia of rotational displacement of the bracket member.

10. The apparatus of claim 1 wherein the base assembly further comprises a base member which is configured and dimensioned for connection to a support stand.

11. An apparatus for guiding a medical instrument comprising:
   a bracket member having a cavity dimensioned and configured to receive at least a portion of a medical instrument;
   a carriage member defining a recess adapted to rotationally support the bracket member;
   a base assembly adapted to be slidably connected to support the carriage member and to move the carriage member into an imaging position;
   a quick release member operatively associated with the bracket and carriage members for removably attaching and detaching the bracket member to and from the carriage member when the carriage member is in the imaging position without losing position and orientation of the carriage member;
   a grid support member adapted to be connected to a first end of the base assembly; and
   a template grid having a plurality of grid apertures and being removably coupled to the grid support member, wherein the base assembly further comprises:
      a handle on a second end of the base assembly for changing the position of the grid support member and the template grid;
      first and second crossbars, each crossbar having first and second apertures;
      first and second elongated, spaced parallel, substantially coextensive sliding rods secured from relative movement by the grid support member and the handle, the first rod being slidable through the first aperture of the first crossbar and the first aperture of the second crossbar and the second rod being slidable through the second aperture of the first crossbar and the second aperture of the second crossbar; and
      an elongated toothed rack connected at opposite ends thereof to the first and second crossbars, the toothed rack slidably engaged with the carriage and being operably engaged with a rotatable gear mounted in the carriage whereby the carriage is moved linearly along the rods and then precisely held in a selected position along the rods in response to rotation of the gear.

12. The apparatus of claim 11 wherein the rack includes a plurality of spaced dimples and the carriage member includes at least one spring loaded plunger, the plurality of spaced dimples interacting with the at least one spring loaded plunger to identify by feel movement of the carriage member.

13. The apparatus of claim 11 wherein the base assembly includes means for eliminating backlash between the carriage member and the base assembly, the means for eliminating backlash comprising at least one height adjusting member to move the rack to vary pressure between teeth of the rack and the gear.

14. An apparatus for guiding a medical instrument comprising:
   a bracket member having a cavity dimensioned and configured to receive at least a portion of a medical instrument:
   a carriage member defining a recess adapted to rotationally support the bracket member;
   a base assembly adapted to be slidably connected to support the carriage member and to move the carriage member into an imaging position;
   a quick release member operatively associated with the bracket and carriage members for removably attaching and detaching the bracket member to and from the carriage member when the carriage member is in the imaging position without losing position and orientation of the carriage member;
   a grid support member adapted to be connected to a first end of the base assembly; and
   a template grid having a plurality of grid apertures and being removably coupled to the grid support member the template grid having first and second spaced surfaces with apertures of the first surface aligned with apertures of the second surface, wherein each aperture is configured and dimensioned to guide elongated objects from the apertures of the first surface to those of the second surface and each aperture is configured to have a wider circumference on one side of the surface to guide the elongated objects.

* * * * *